United States Patent [19]

Maggard

[11] Patent Number: 5,349,188

[45] Date of Patent: * Sep. 20, 1994

[54] NEAR INFRARED ANALYSIS OF PIANO CONSTITUENTS AND OCTANE NUMBER OF HYDROCARBONS

[75] Inventor: Steven M. Maggard, Huntington, W. Va.

[73] Assignee: Ashland Oil, Inc., Ashland, Ky.

[*] Notice: The portion of the term of this patent subsequent to Oct. 16, 2007 has been disclaimed.

[21] Appl. No.: 506,391

[22] Filed: Apr. 9, 1990

[51] Int. Cl.$^5$ .............................................. G01N 21/35
[52] U.S. Cl. ..................................... 250/339; 250/343
[58] Field of Search ........................ 250/339, 343, 340

[56] References Cited

U.S. PATENT DOCUMENTS

| | | | |
|---|---|---|---|
| 3,505,857 | 4/1970 | Jenkins | 73/61 |
| 4,277,326 | 7/1981 | Schlasberg et al. | 208/263 |
| 4,323,777 | 4/1982 | Baskins | 250/339 |
| 4,433,239 | 2/1984 | Thompson | 250/255 |
| 4,448,530 | 5/1984 | Schmitt et al. | 356/326 |
| 4,591,718 | 3/1986 | Amer | 250/339 |
| 4,800,279 | 1/1989 | Hieftje et al. | 250/339 |
| 4,963,745 | 10/1990 | Maggard | 250/339 |
| 5,131,746 | 7/1992 | O'Rourke et al. | 356/436 |

FOREIGN PATENT DOCUMENTS

| | | |
|---|---|---|
| 285251 | 10/1988 | European Pat. Off. ............ 250/339 |
| 0304232 | 11/1988 | European Pat. Off. . |
| 2217838 | 11/1989 | United Kingdom . |

OTHER PUBLICATIONS

Louw et al., "A Simple Directly Combined Gas Chromatographic Infrared Spectrometric System for Identification of Low, Molecular Weight Hydrocarbons", Applied Spectroscopy, 29 (1), 1975, pp. 15–24.

Maris et al, "Nonlinear Multicomponent Analysis by Infrared Spectrophotometry", Anal. Chem., 55 (1983), pp. 1694–1703.

"Determination of Carbon–Hydrogen Groups in High Molecular Weight Hydrocarbons", A. Evans & R. R. Hibbard, Analytical Chemistry, vol. 23, No. 11, Nov. 1951, pp. 1604–1610.

"Nondestructive Analytical Proc. for Simultaneous Estimation of the Major Classes of Hydrocarbon Constituents of Finished Gasolines," Kelly et al., Anal. Chem. 1990, 62, pp. 1444–1451.

"Advances in Near Infrared Analyzer Technology" Dr. H. Mark & Dr. G. Kemeny, Feb. 1991 Chemical Processing, pp. 54–58.

LT Appl. Note, Industry: Petroleum, "Determination of Octane Number by NIR," LT Industries, Rockville, Md.; undated.

*Primary Examiner*—Carolyn E. Fields
*Attorney, Agent, or Firm*—Richard C. Willson, Jr.

[57] ABSTRACT

Certain selected wavelengths in the near infrared spectra permit analysis of weight percent, volume percent, or even mole percent of each component, e.g. PIANO (paraffin, isoparaffin, aromatic, napthenes, and olefins), octane (preferably research, motor or pump), and percent of various hydrocarbons, e.g. alpha olefins. Analysis can be nearly continuous analysis on-line or at-line, as well as batch analysis, e.g. in a quality control laboratory. Preferably the NIR data is converted to a second derivative of the spectra and multiple linear regression performed to model the individual PIANO concentrations, and to predict physical properties of fuel blending components, e.g. research octane of reformate, etc.

36 Claims, 8 Drawing Sheets

NEAR INFRARED ANALYSIS OF PIANO CONSTITUENTS AND OCTANE NUMBER OF HYDROCARBONS

CROSS REFERENCE TO RELATED APPLICATIONS

Cross references to related application: U.S. patent application 402,959, filed Sep. 1, 1989 now U.S. Pat. No. 4,963,745, issued Oct. 16, 1990 relates to the general field of the present invention.

BACKGROUND OF INVENTION

I. Field of the Invention

The present invention relates to techniques of analysis, particularly of hydrocarbon and substituted hydrocarbon mixtures, generally classified in U.S. Class 250.

II. Description of the Prior Art

Many prior teachings of the determination of the individual components of paraffins, isoparaffins, aromatics, napthenes, and olefins (PIANO) have been taught in prior literature and patents. A preferred prior technique is gas chromatography, wherein a sample is injected into an absorbant column swept by an elutriating inert gas, e.g. helium, and the elapsed time for arrival at the end of the column is measured for each of the components, e.g. by a flame ionization detector, thermal conductivity detector, or other detector.

Conventionally, the percents of each of the individual compounds detected by gas chromatography are grouped under their respective generic classifications in the PIANO classification system, and the relative percentage of each of the components paraffins through olefins is determined in weight percent, volume percent, or mole percent as required. An example of this procedure is that taught by Analytical Automation Specialists, Inc., "The Detailed Analysis of Petroleum Naphthas, Reformates, Gasoline and Condensates by High-Resolution Gas Chromatography", Operators Manual, P.O. Box 80653, Baton Rouge, La. 70898. Also available in AAS (Analytical Automated Systems) PIANO Software Package, Sievers Research PIANO Software Package.

Recently, near-infrared (NIR) spectrophotometric analysis has been used to determine baking quality of flour, digestibility of forages, and other physical properties of samples, e.g. in U.S. Pat. No. 4,800,279 to Hieftje, Honigs, and Hirschfeld, and a number of the references cited therein.

Other NIR analysis techniques are taught in J. Prakt. Chem., 317(1), 1-16 by Bernhard and Berthold, who perform structural group analysis of mixtures of saturated and aromatic hydrocarbons, and in the quantitative analysis of benzene-toluene-paraffin mixtures in the near-infrared by Leimer and Schmidt in Chem. Tech. (Leipzig), 25(2), 99-100.

Near-infrared spectroscopy of hydrocarbon functional groups was performed by Tosi and Pinto, Spectrochim ACTA, Part A, 28(3), 585-97, who examined 50 linear and branched paraffins and related the absorbtivities to the concentration of the groups such as $CH_3$ and $CH_2$.

Ultraviolet and Near-infrared analysis of mixtures of aromatics is taught by Schmidt in Erdoelkohle, Erdgas, Petrochem., 21(6), 334-40, who sought to determine concentration of specific compounds, not the groups (aromatic, etc.) measured by this invention, and used different wavelengths.

Kelly, Barlow, Jinguji and Callis of the University of Washington, Seattle, (Analytical Chem. 61, 313-320,) found gasoline octane numbers could be predicted from near infrared absorbance in the range 660-1215 nanometers (nm). They found best correlation between absorbance and octane number to occur at 896, 932 and 1164 nm for research octane number, 930, 940 and 1012 nm for motor octane number, and 896, 932 and 1032 nm for pump octane number. Kelly does not teach PIANO analysis, and only uses the short wavelength near-infrared, 660-1220 run, but did determine the aromatic, olefin, and saturate (paraffins plus isoparaffin) content of gasolines. However, Kelly used a very limited number of samples (nine) and restricted their measurements to the short wavelength near infrared (660-1220 nm), unlike the present invention. Furthermore, they did not disclose which wavelengths correlated with aromatic, olefin, or saturate concentrations. Example 6 compares this Kelly work. Thus Kelly does not enable one skilled in the art to practice the present invention nor to attain its advantages.

None of above teach PIANO analysis of the more complex mixtures routinely encountered in petroleum refineries. Such mixtures almost always contain both aromatics and olefins which are generally thought to have overlapping absorbance wavelengths in the mid-infrared region, suggesting that their overtones and combination bands in the near-infrared region would also overlap, and preclude determination of their individual concentrations in the mixtures.

Such mixtures are often very complex; gasoline mixtures frequently contain over 300 compounds.

Also, individual molecular groups found (e.g. methylene) in napthenes, are also found in paraffins and also in isoparaffins, as well as in substituted aromatic compounds, and also in olefins, further compounding the difficulty of analyzing for concentration of individual PIANO components.

SUMMARY OF THE INVENTION

I. General Statement of the Invention

The present invention utilizes a combination of selected NIR wavelengths in which measurements of absorbance are made and combines these with multiple regression analysis and modeling to differentiate the concentration of individual PIANO components.

FIG. 1 is a plot of the second derivative of absorbance versus wavelength for a simulated complex mixture. The simulation is accomplished by super-imposing a plot of alpha-olefins on plots of paraffins, isoparaffins, aromatics and napthenes. As can be seen, olefins have several characteristic wavelength ranges which can be used to determine their concentration. It can be seen from FIG. 1 that the olefins should be distinguishable from the other PIANO components, isoparaffins, paraffins, etc. in the wavelength region of 2050 to 2250 nm.

Complex mixtures, such as gasolines and reformates, have 5 total degrees of freedom for a PIANO analysis by NIR (one for each of the PIANO components). Since the degrees of freedom for a mathematical model must be less than the total number of degrees of freedom, a maximum of four wavelengths can be used in the model. However, it should be noted that some experimenters might wish to use more or less wavelengths. Each PIANO constituent has its own model in the present invention. In the case of paraffins and isoparaffins, no characterizing wavelength has been found in the near infrared region because of overlapping absorbances of the other PIANO constituents, and therefore their concentrations must be solved for using the four degrees of freedom and by using four different wavelengths. Experimentally it has been found useful to isolate portions of the near infrared spectra where paraffins and isoparaffins can be distinguished. The following wavelengths are most useful for the determination of paraffin and isoparaffin concentrations: 880–974, 1152–1230, 1320–1380, 1470–1578, 1614–1644, 1746–1810, 1940–2000, and 2058–2130 run. For the case of aromatics, napthenes, and olefins, however, it is possible to identify characteristic portions of the spectra where these constituents can be identified as shown in FIGS. 1–5. As a result of this, only three degrees of freedom are needed to determine the concentration of each of these constituents, and hence only three wavelengths are needed. Because it is possible to isolate characteristic wavelengths for these constituents, it ensures that the predicted concentrations are truly related to the PIANO constituent of interest.

II. Utility of the Invention

This invention will find greatest application in the petroleum refining industry. For example, it can be used to monitor the aromatic content of gasolines, diesel fuel, and jet fuel. Another potential application is to feed the aromatic and olefin concentrations of gasoline or gasoline blending streams into a blending program such as Ashland Petroleum's BOSS (Blend Optimization and Scheduling System), Chevron's GINO (Gasoline In-Line Optimization), Oil Systems, Inc., MGBlend, or other similar blending optimization programs. Other applications of the invention include various catalytic processes such as catalytic reforming where a knowledge of feedstock composition and product composition could be used to determine reactor severity and in the optimization of the unit. PIANO composition of fluid catalytic cracking bottoms is another application. The characteristic PIANO wavelengths can also be used to make predictions of octanes. For example, wavelengths which are indicative of aromatic concentration can also be used to predict the octane of reformates since it is the aromatic content which predominately determines the octane. Similarly alpha-olefin content was found to be highly correlated with the motor octane of Ashland summer blended gasolines.

There are also an enormous number of applications of PIANO analyses outside of the petroleum industry. For example, the monitoring of alpha-olefin concentration during cationic polymerization reactions in the detergent industry. Also the invention could be used to monitor the purity of various streams, the concentration changes which occur during a chemical reaction, and even impurity concentrations of PIANO constituents.

Signal Processing

As those skilled in the art will be aware, the absorbance signal from the measurement of the characteristic PIANO bands, used either solely or in conjunction with other bands, will preferably be mathematically processed to provide derived signals which are indicative of the concentrations (or property) being measured. Preferred techniques for mathematical processing are absorbance base-line offset corrected absorbance data; taking the first, second, third, fourth or higher derivative of the absorbance spectrum; the technique of dividing the absorbance at one wavelength by another; spectral subtraction; and various combinations of these mathematical techniques. Also valuable are the well-known curve fitting techniques of Savitsky-Golay and Kubelka-Munk, and N-point smoothing (signal averaging). Other types of statistical data treatment are also possible such as partial least squares (PLS), Gauss-Jordan Row reduction, etc.

By equivalent to weighting constant, we mean to include among other techniques known to the art the wavelength coefficients of partial least squares regression and principal component regression and the constants obtained from the Gauss-Jordan row reduction algorithm. (See Harald Martens and Tormod Naes, Multivariate Calibration, John Wiley & Sons; New York, 1989 [ISBN 471-90979-3], and Honigs, D. E., Heiftje, G. M.; Hirschfeld, T., Applied Spectroscopy, 38(3), 1984, p. 317.) Also any constant obtained from any statistical calibration used to calculate values for unknown samples.

Octane Measurement

The techniques of the present invention are also highly useful for the objectives of aforementioned co-pending U.S. Ser. No. 402,959, filed Sep. 1, 1989 relating to the determination of research, motor and pump octane (also including cetane number of diesel fuels). Example 4 shows the invention predicting research octane number of reformate.

Measuring octane number, including any other measure of knock avoidance, of fuels by near infrared range spectroscopy, the present invention takes the octane number by:
  (a) measuring at at least one wavelength, the near infrared absorbance in the bands of:
    1. for napthenes: 1672–1698 and/or 1700–1726 nanometers (nm);
    2. for olefins: 1622–1650 and/or 2064–2234 nm;
    3. for aromatics: 1092–1156 and/or 824–884 and/or 1656–1692 nm;
    4. for paraffins and isoparaffins: 880–974, 1152–1230, 1320–1380, 1470–1578, 1614–1644, 1746–1810, 1940–2000, and/or 2058–2130 nm.
  (b) taking each of the absorbances measured, or a mathematical function thereof,
  (c) performing multiple regression analysis partial least squares analysis, or other statistical treatment using the above absorbances or functions as individual independent variables,
  (d) assigning and applying weighting constants or their equivalents to said independent variables,
  (e) applying the above steps using known compositions to calibrate the instrument and determine said weighting constants or equivalents,
  (f) repeating said steps with unknown compositions, applying the weighting constants or equivalents determined during said calibration with known compositions.

The flow may flow substantially intermittently or continuously past the point where the measurements are being made. The mathematical function may be a first, second, or third, etc. derivative of said absorption of said band being measured, the fuel may preferably be a gasoline blending stream, and the octane measured may preferably be research octane, more preferably motor octane, and most preferably pump octane.

As discussed briefly below and in the copending application aforementioned, the signal may control a fuel blending system feeding blending components having different octane numbers into a common zone, whereby a fuel product having a desired octane is produced.

Analytical Equipment

Near Infrared spectrometers, Fourier Transform near infrared spectrometers, and modified IR spectrometers of conventional design may be used with the invention. Preferred modes of operation are transmission, reflectance, and transflectance. Suitable spectrometers are the NIR Systems Model 6500; LT Industries Model 1200; and the Guided Wave Model 300 Series. The spectrometer can be operated in a quality control lab, on a batch basis (receiving signals, e.g. by a sample feeding arrangement), or, more preferably, on a continuous basis in which the fluid to be measured flows through a cell or in which a probe immersed in the flowing fluid transmits optically through a fiber-optic cable to the spectrophometer. The techniques for sampling, measuring, and signal processing can be conventional and are well known to those skilled in the art.

Blending Systems

Blending systems for use with the present invention to provide blends having desired PIANO analyses can be of conventional design, usually involving the use of proportioning pumps or automatic control valves which control the addition rate for each of a series of components fed from different tanks or other sources. A computer receiving the output signal from the spectrophotometer can readily process the information to not only provide the target PIANO analysis or octane number in the finished blended hydrocarbon, e.g. gasoline, but also to provide the target blend at minimum cost, given the relative costs and octane or PIANO enhancement values of the components being fed to the blending system.

The present invention permits the determination of PIANO components which have previously been determined only by laboratory analysis or by relatively long gas chromatography techniques. The invention permits this determination of different components to be made simultaneously and nearly continuously, providing on-line (or at-line) analysis without the need to return samples to control labs in refineries.

DESCRIPTION OF THE PREFERRED EMBODIMENTS

Example 1

The Invention Measuring the PIANO

Figure 1:
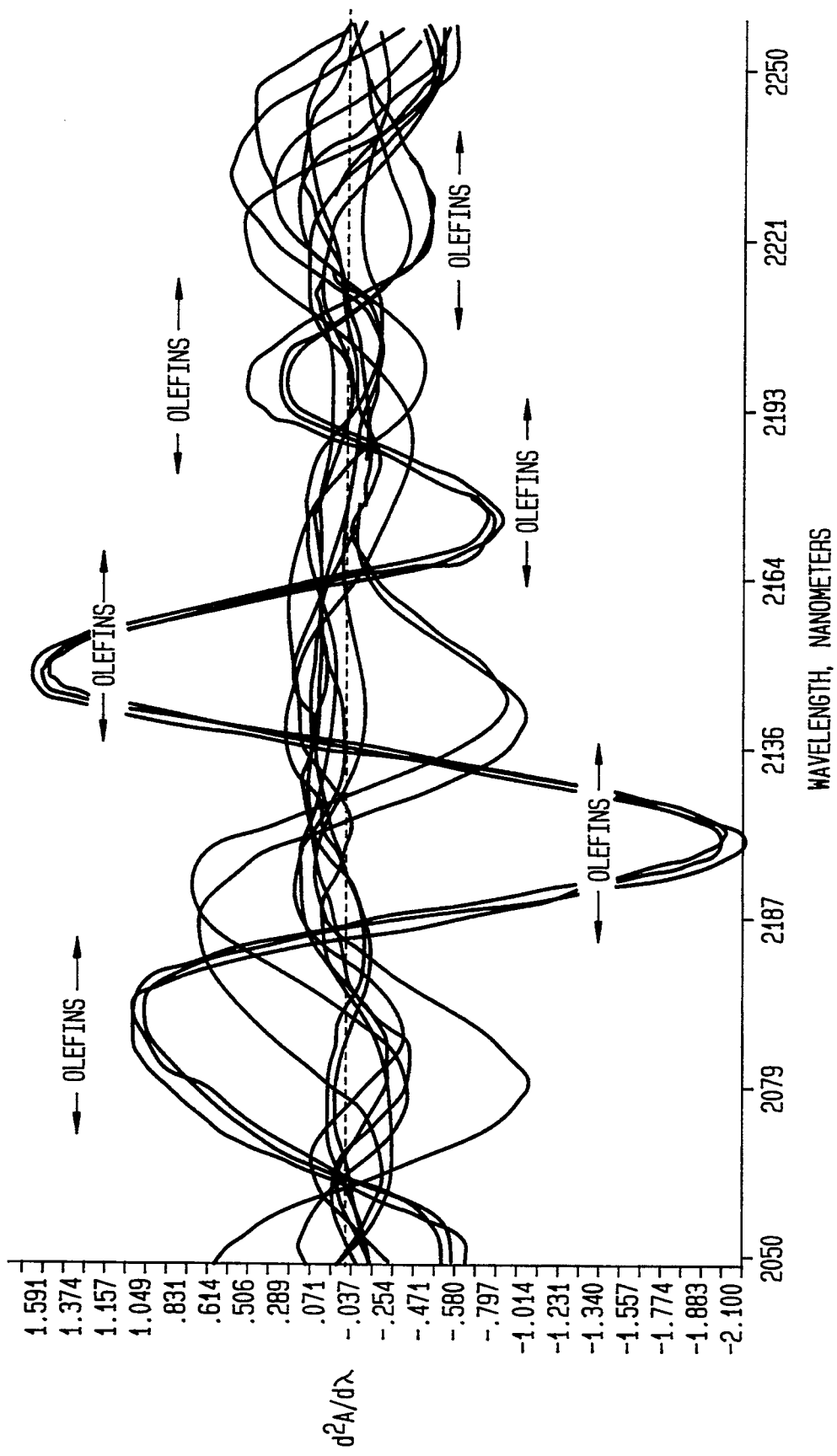
FIG. 1 is a plot of the second derivative of absorbance versus wavelengths for olefins superimposed on other PIANO constituents from 2050 to 2250 nm.
Figure 2:
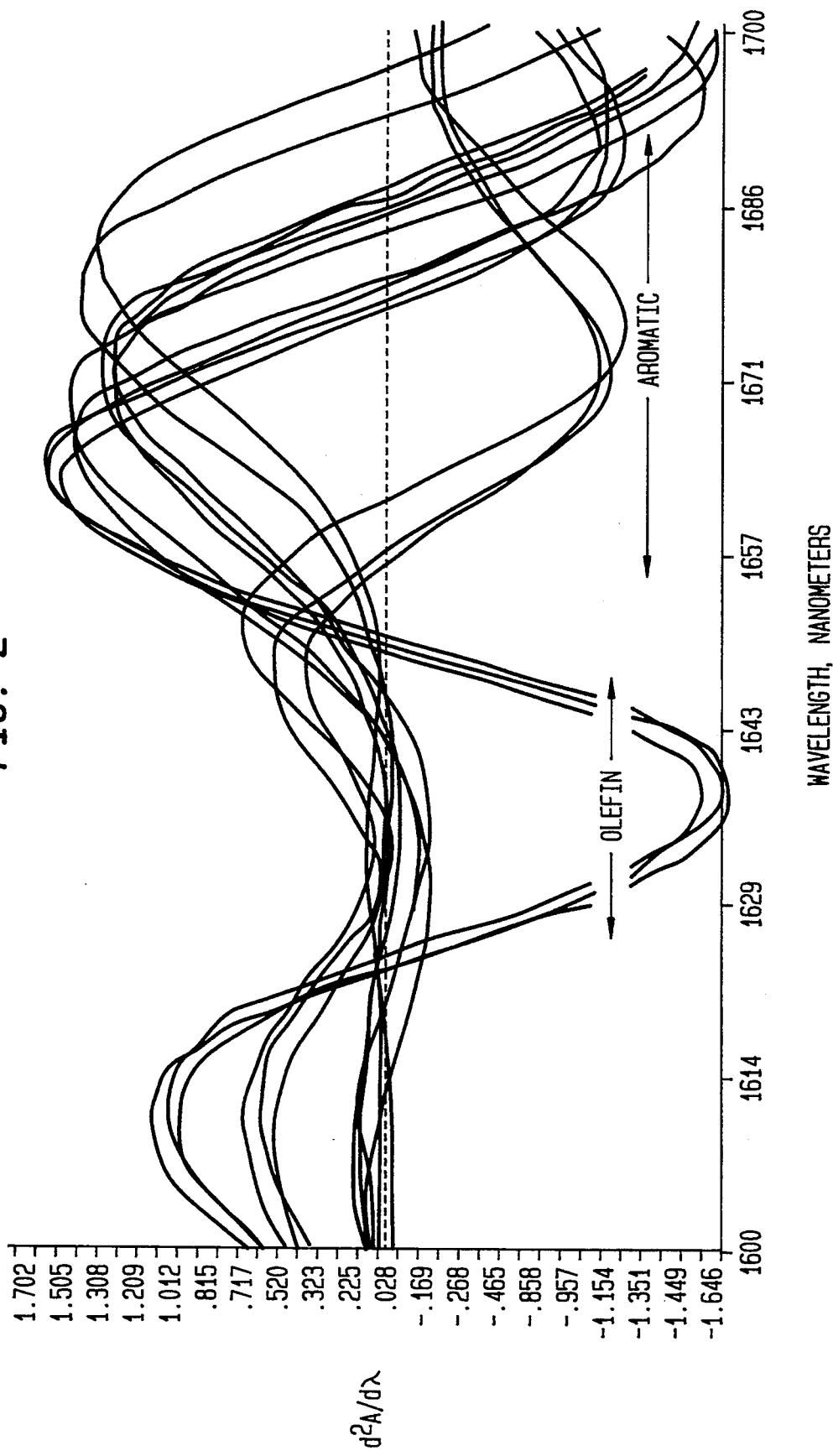
FIG. 2 is a similar plot from 1550 to 1750 nm. An aromatic band is also present in this Figure.
Figure 3:
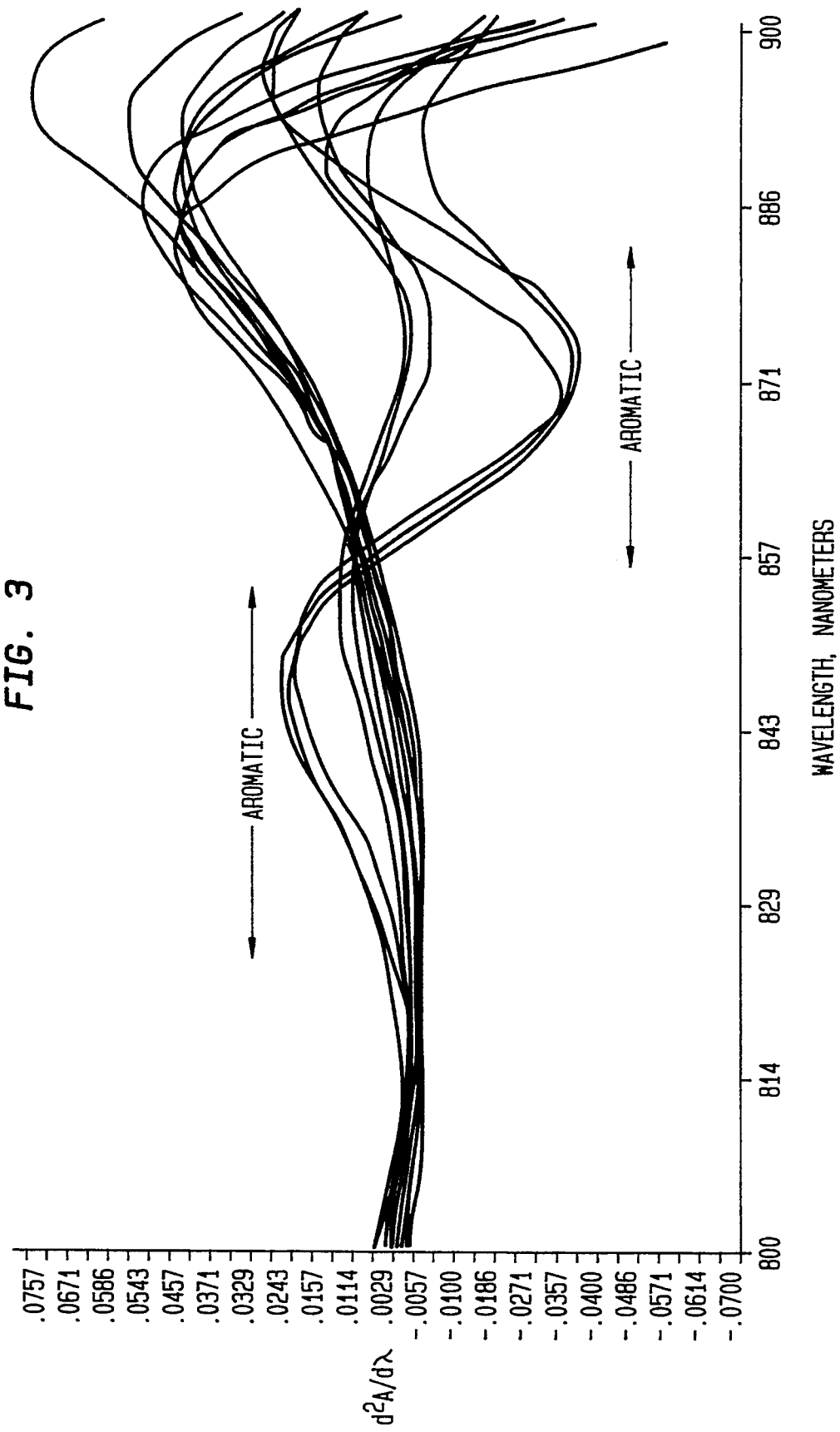
FIG. 3 is a similar plot showing aromatics superimposed on other PIANO constituents from 800 to 900 nm.
Figure 4:
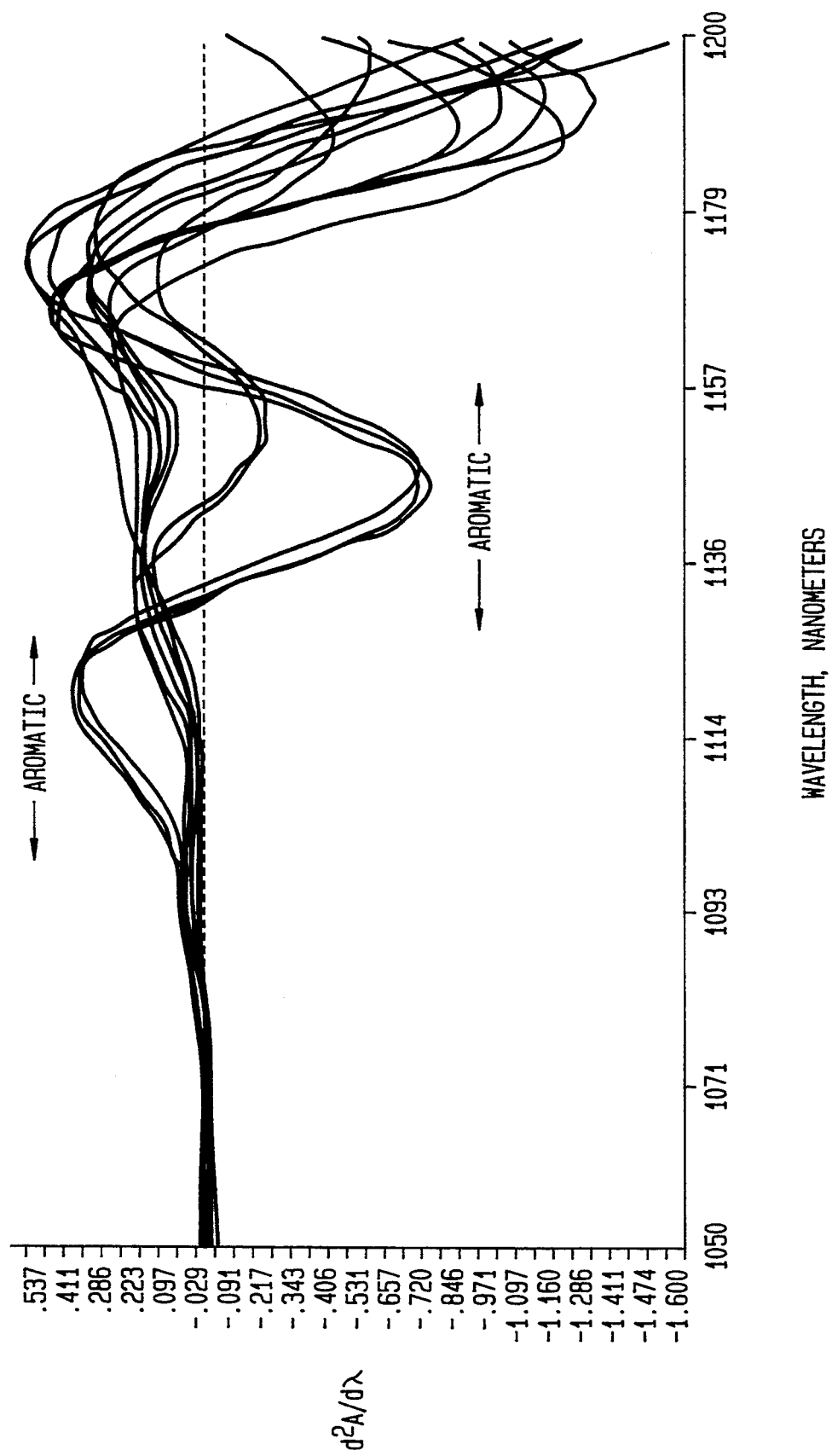
FIG. 4 is a similar plot showing aromatics superimposed on other PIANO constituents from 1050 to 200 nm.
Figure 5:
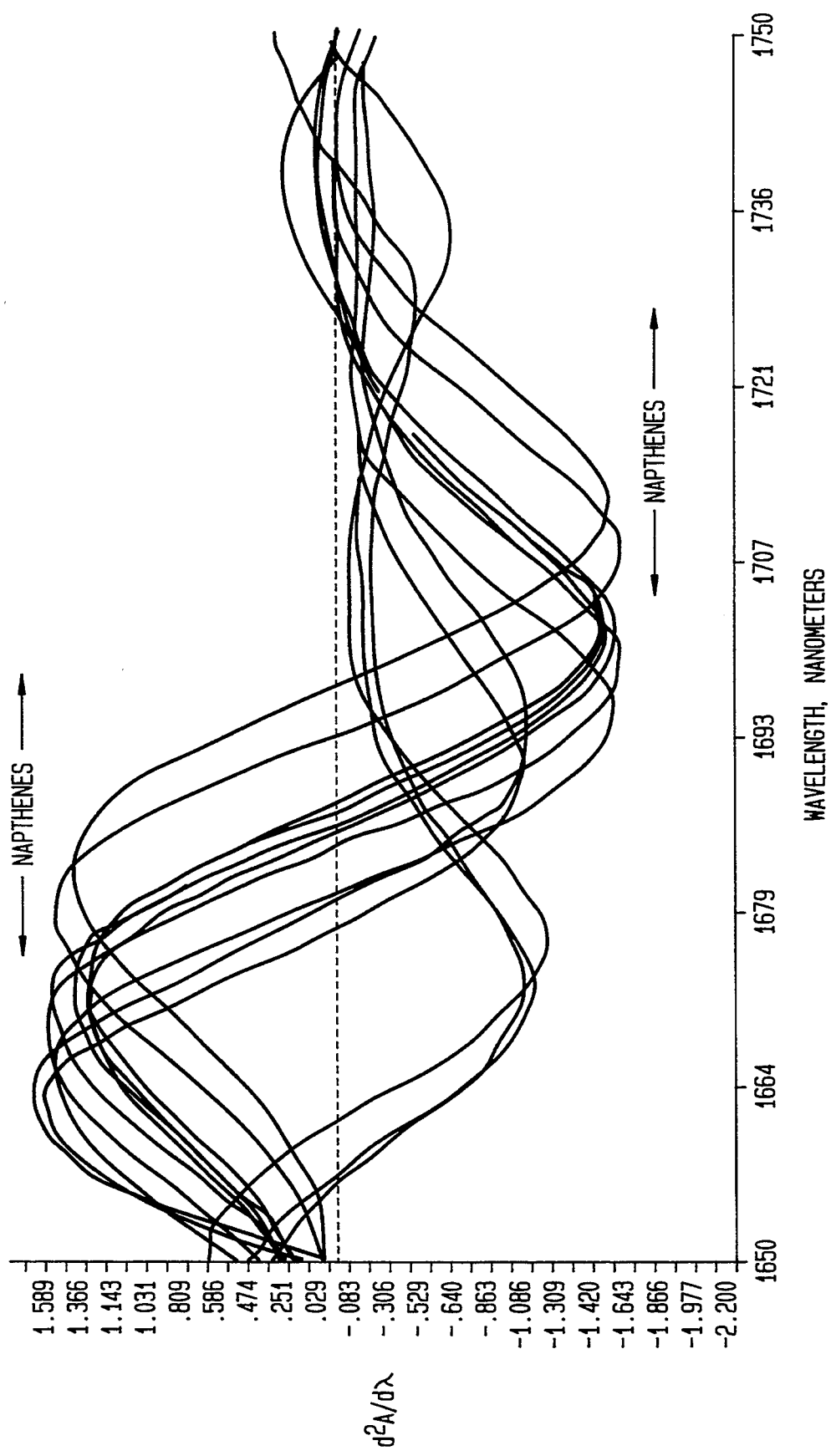
FIG. 5 is a similar plot showing napthenes superimposed on other PIANO constituents from 1650 to 1750 nm.

Mixtures containing PIANO components as follows are analyzed according to the techniques of the present invention:

| | |
|---|---|
| paraffin | 8.86–32.7 % by volume |
| isoparaffin | 19.1–51.8 |
| aromatics | 13.0–68.0 |
| napthenes | 0.509–21.6 |
| olefins | 0.00–17.7 |

The samples include gasolines, stabilized reformates, unstabilized reformates, naphtha, and catalytically cracked bottoms.

The apparatus is an NIR System Model 6500 Near Infrared Spectrophotometer measuring approximately 200 samples of hydrocarbons each containing PIANO components. The wavelengths used and the range of volume percents are shown in Table 1. Approximately 50 of the samples were separated out as a calibration set, selected so as to represent a increasing concentration of each of the PIANO constituents so that the entire range was covered.

A multiple regression analysis was performed on the second derivative of the absorbances measured at the indicated wavelengths. The regression coefficients are as shown in Table 2, with the multiple coefficients of correlation being as shown in Table 1.

The standard errors of the estimate (calculated by well-known statistical techniques) for this calibration set are shown in Table 1.

The remaining 150 samples are used as a prediction set (for prediction of PIANO in unknown samples). Again, the second derivative of the absorbances are used as the independent variables in a multiple regression analysis using the weighting constants determined from the calibration set and shown in Table 2, using NIR System's computer program (NIR Spectral Analysis Software) for multiple regression analysis supplied with the apparatus, though SAS or other well-known statistical programs could be used instead. These programs multiply the second derivative of each absorbance at each wavelength by its respective weighting constant and sum the products and the regression constant to provide a weighted value which is characteristic of the predicted percent of each respective PIANO component, e.g. the standard error of prediction is shown in the far right column of Table 1.

Comparing the standard error of estimate with the standard error of prediction, it can be seen that the actual standard error of prediction shows excellent correlation between the model and the actual concentrations.

TABLE 1

Results of PIANO Analysis of Stabilized Reformates, Unstabilized Reformates, Gasolines, Reformer Feed (Naphtha), and Catalytically Cracked Bottoms

| Component | Wavelengths, nm | Range of Values Vol. % | Mult. Corr. | Std Error of Est. Vol. % | Std Error or Pred. Vol. % |
|---|---|---|---|---|---|
| Paraffins | 1468,1934,1986 & 2058 | 8.86–32.7 | 0.9837 | 0.869 | 0.915 |
| Isoparaffins | 1384,1648,1230 & 1062 | 19.1–51.8 | 0.9903 | 1.18 | 1.02 |
| Aromatics | 2062,1148,1908 | 13.0–68.0 | 0.9994 | 0.540 | 0.593 |
| Napthenes | 1710,1428,1496 | 0.509–21.6 | 0.9839 | 0.800 | 0.591 |
| Olefins | 2114,2148,1638 | 0–17.7 | 0.9802 | 1.04 | 0.467 |

TABLE 2

Multiple Regression Coefficients for Prediction of PIANO Concentrations and Octanes

| | PIANO Analysis of Reformates, Catalytically Cracked Bottoms, Naphtha, & Gas. | PIANO Analysis of Reformates, (Stab. and Unstab.) | Motor Octane Number of Gasolines | Research Octane Number of Reformates |
|---|---|---|---|---|
| Regression Constant | | | | |
| Paraffins | −41.45 | −1.422 | | |
| Isoparaffins | −4.244 | −99.99 | | |
| Aromatics | 9.474 | 91.76 | 78.28 | 288.6 |
| Napthenes | 11.10 | 9.645 | | |
| Olefins | 17.48 | −18.82 | | |
| Regression Coefficient (wavelength) | | | | |
| Paraffins | 721.3 (1468) | −3878 (1288) | | |
| Isoparaffins | −180.5 (1384) | 1261 (1330) | | |
| Aromatics | 172.3 (2062) | −14.56 (1148) | 14.96 (1220) | 80.10 (1220) |
| Napthenes | −20.61 (1710) | −207.1 (1420) | | |
| Olefins | −33.42 (2114) | −48.51 (1636) | | |
| Regression Coefficient (wavelength) | | | | |
| Paraffins | −143.7 (1934) | 716.4 (1468) | | |
| Isoparaffins | 24.06 (1648) | −4562 (858) | | |
| Aromatics | −67.6 (1148) | 161.5 (2060) | −8.474 (2092) | −185.2 (1130) |
| Napthenes | −213.7 (1428) | 11.91 (1678) | | |
| Olefins | −29.94 (2148) | 1448 (1312) | −8.474 (2092) | |
| Regression Coefficient (wavelength) | | | | |
| Paraffins | 192.8 (1986) | 716.4 (1468) | | |
| Isoparaffins | −275.8 (1230) | 147.1 (1190) | | |
| Aromatics | −95.73 (1908) | 83.40 (1196) | — | −4493 (1572) |
| Napthenes | −337.3 (1496) | 500.4 (1538) | | |
| Olefins | −49.41 (1638) | −103.9 (1454) | | |
| Regression Coefficient (wavelength) | | | | |
| Paraffins | −105.2 (2058) | 133.9 (2048) | — | — |
| Isoparaffins | 4716 (1062) | −2478 (1020) | — | — |

Example 2

PIANO Analysis of Reformate by the Invention

Figure 6:
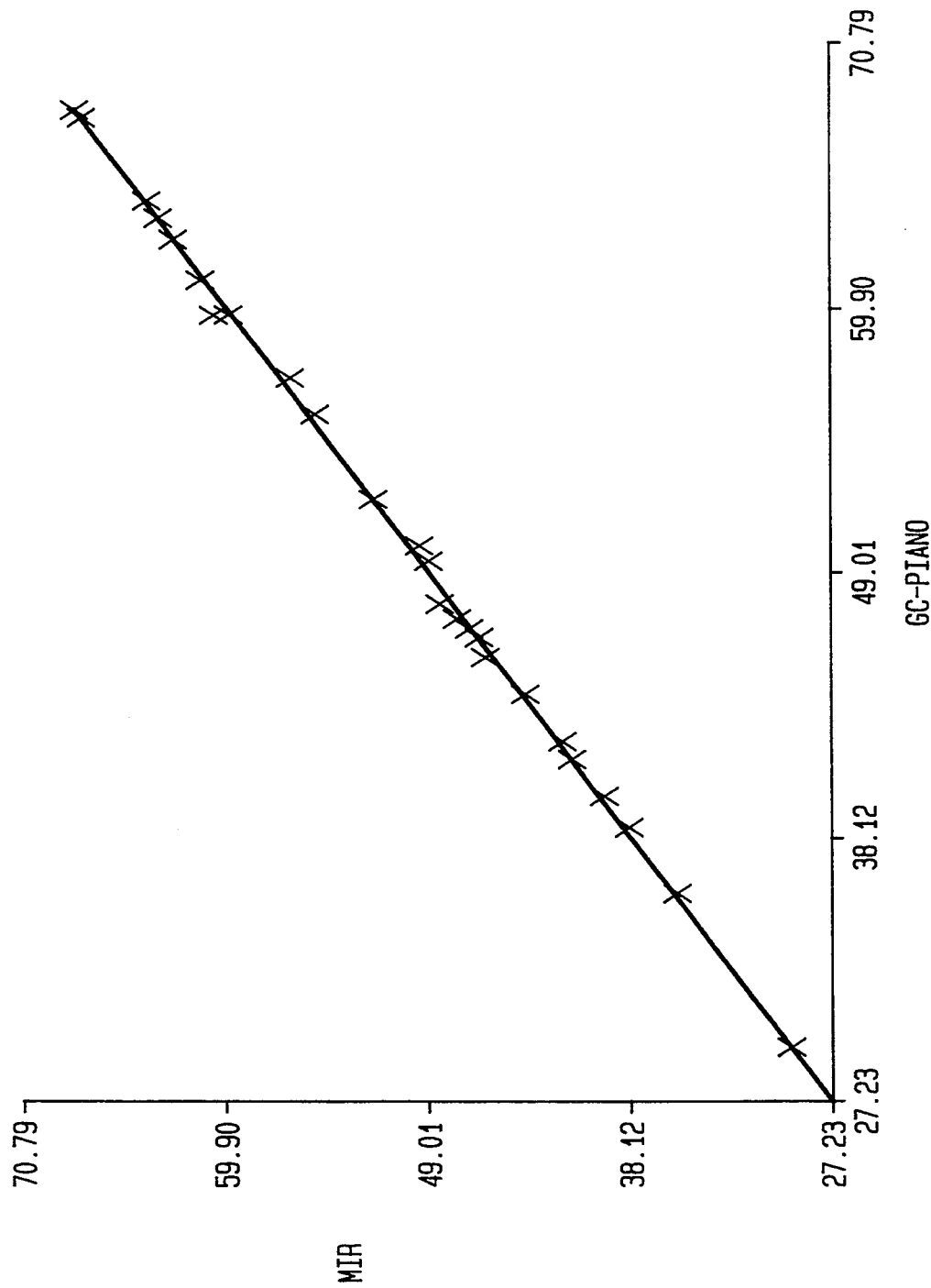
FIG. 6 shows the volume percent aromatics as measured by gas chromatography (GC-PIANO) versus the volume percent predicted according to the present invention in Example 2.
Figure 7:
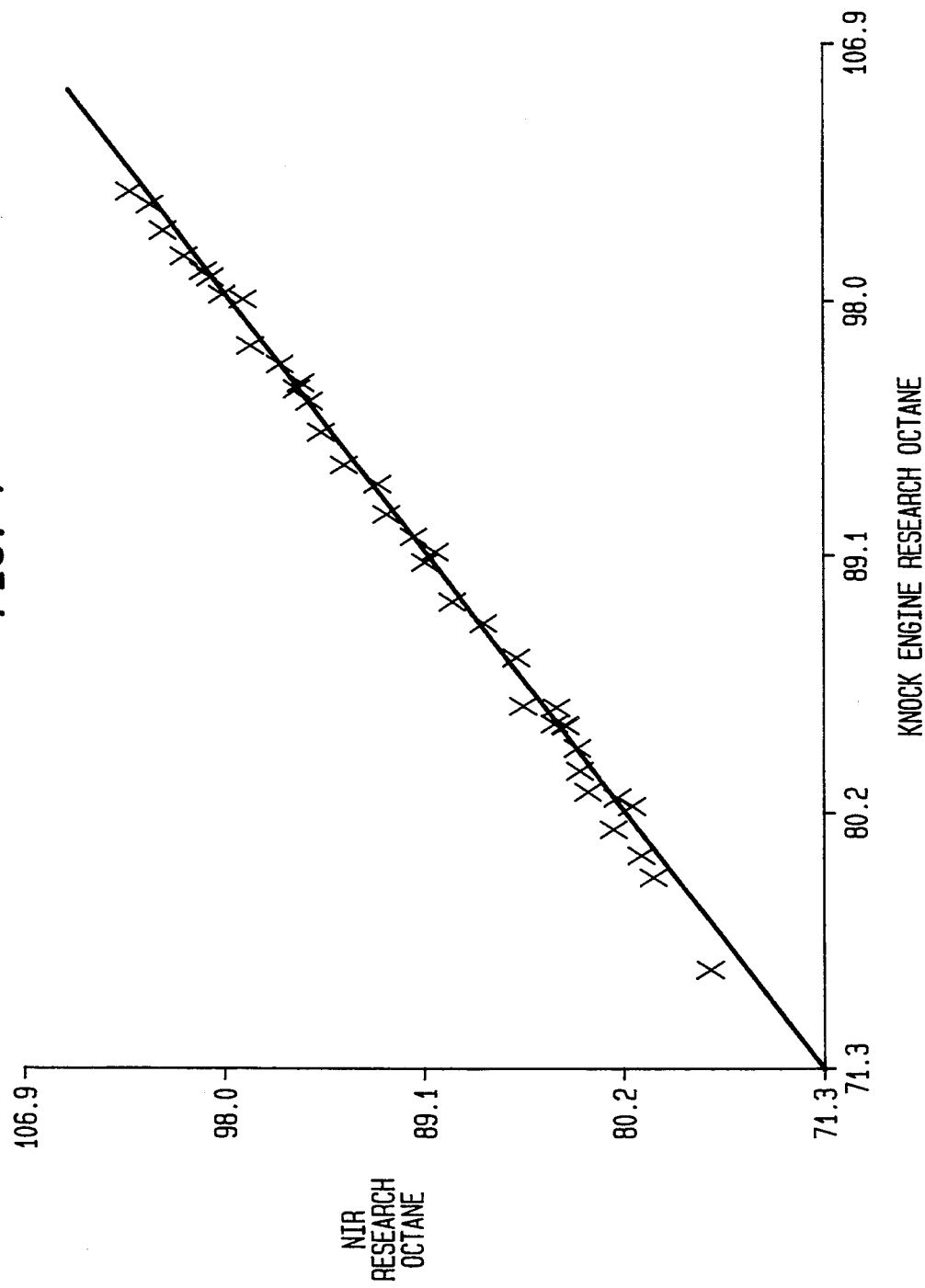
FIG. 7 is plot of reformate research octane predicted by NIR versus a knock engine from Example 4.
Figure 8:
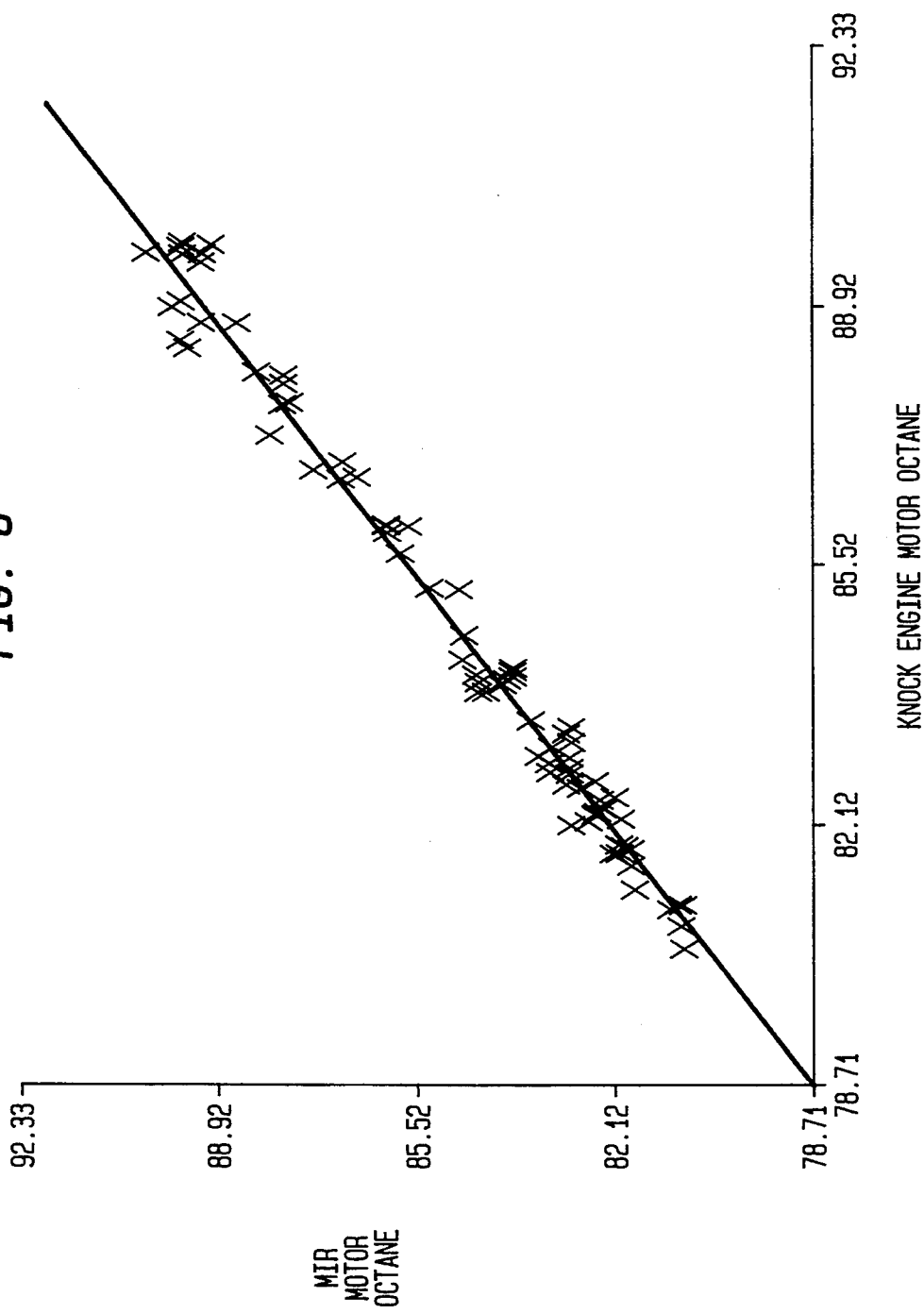
FIG. 8 is a plot of motor octanes predicted by the present invention versus a knock engine from Example 5.

When the procedure of Example 1 is repeated on just the stabilized and unstabilized reformate samples, a much greater level of accuracy can be achieved. For example, approximately 25 reformate samples were selected to be used in a calibration set. They were chosen on the basis that they uniformly covered the range of PIANO constituent concentrations. Multiple linear regression was performed on the calibration set using the wavelengths shown in Table 3. The regression coefficients and constant are shown in Table 2. FIG. 6 is a plot of the actual volume percent of aromatics (determined by GC-PIANO) versus the value predicted by the present invention for the calibration data. This data was then used to predict the PIANO concentrations of approximately 125 unknowns. Excellent agreement can be seen between the standard errors of the estimate and the standard errors of prediction in Table 3. High correlations are also observed with the exception of the olefins. This is a result of the low range of olefins in the samples in spite of their low errors of prediction.

TABLE 3

Results of PIANO Analysis of Stabilized and Unstabilized Reformates

| Component | Wavelengths, nm | Range of Values Vol. % | Mult. Corr. | Std Error of Est. Vol. % | Std Error or Pred. Vol. % |
|---|---|---|---|---|---|
| Paraffins | 1288,1468,890 | 8.86–21.5 | 0.9889 | 0.465 | 0.492 |

TABLE 3-continued

Results of PIANO Analysis of Stabilized and Unstabilized Reformates

| Component | Wavelengths, nm | Range of Values Vol. % | Mult. Corr. | Std Error of Est. Vol. % | Std Error or Pred. Vol. % |
|---|---|---|---|---|---|
| | & 2048 | | | | |
| Isoparaffins | 1330,858,1190 & 1020 | 19.1–40.0 | 0.9964 | 0.666 | 0.774 |
| Aromatics | 1148,2060,1196 | 35.9–68.0 | 0.9995 | 0.342 | 0.494 |
| Napthenes | 1420,1678,1538 | 0.509–8.83 | 0.9875 | 0.296 | 0.359 |
| Olefins | 1636,1312,1454 | 0–3.89 | 0.7803 | 0.627 | 0.418 |

Example 3
The Invention Using Partial Least Squares Analysis

When the procedure of Example 1 is repeated on the same samples but substituting partial least squares regression analysis for the multiple regression analysis utilized in Example 1, results are obtained which are shown in Table 4.

The predictions are not as accurate as those of Example 1. An entire area of the spectrum is generally used rather than single wavelengths. For example, for aromatics, the wavelength range from 826 to 1152 nm is used using four latent variables. The four latent variables correspond to the four degrees of freedom for the model. The calibration set for this example includes approximately 50 stabilized and unstabilized reformates, naphthas, and catalytically cracked bottoms and gasolines and the results appear in Table 4. The predictions set include approximately 150 samples of similar hydrocarbon mixtures. Four latent variables were used for each model.

Referring to Table 4, excellent agreement between the standard errors of prediction and the estimate can be seen, showing that the wavelength ranges are indeed highly correlated with their respective PIANO group constituents. It should be possible to obtain even better correlations if the wavelength ranges are further optimized by including other portions of the NIR spectrum.

TABLE 4

Results of PIANO Analysis by Partial Least Squares Analysis for Stabilized and Unstabilized Reformates, Naphtha, Gasolines

| Component | Wavelength Range, nm | Mult. Corr. | Std Error of Est. Vol. % | Std Error or Pred. Vol. % |
|---|---|---|---|---|
| Aromatics | 826–1692 | .995 | 1.63 | 1.16 |
| Napthenes | 1672–1726 | .973 | 1.03 | 0.770 |
| Olefins | 1622–2200 | .989 | 0.771 | 0.603 |
| Paraffins | 880–2130 | .957 | 1.39 | 1.53 |
| Isoparaffins | 880–2130 | .975 | 1.85 | 1.18 |

Example 4
The Invention Predicting Research Octane Number of Reformate

Applying the process of Example 2 to about 150 samples of a reformate produced by a bench scale reformer operating on Arabian light naphthas, the samples are divided into a calibration set of approximately 50 samples and a prediction set of about 100 samples. The calibration set is chosen to cover a range of research octane numbers from 73 to 102. Multiple regression is preformed on the second derivatives of the absorbances at 1220, 1130 and 1572 nanometers, and a multiple correlation of 0.998 is observed. The calibration samples show a standard error of estimate of 0.505 research octane numbers, and the prediction set shows a standard error of prediction of 0.526 research octane units. This compares favorably to ASTM method D2699 for operation of knock engines which shows a standard error of greater than 0.6 research octane numbers (error estimates are not given for below 80 research octane numbers). The results of the analysis are summarized in Table 5.

TABLE 5

Octane Results for Reformates and Gasolines

| Substance | Type of Octane | Range of Values Octane No. | Mult. Corr. | Std Error of Est. Vol. % | Std Error of Pred. Vol. % | ASTM Allow. Error, Octane No. |
|---|---|---|---|---|---|---|
| Reformate | RON | 73–102 | 0.9980 | 0.505 | 0.526 | >0.6 |
| Gasoline | MON | 80–91 | 0.9924 | 0.362 | 0.412 | 0.6 |

Example 5

139 gasoline samples each analyzed for motor octane number by ASTM D2700, and with the samples uniformly covering the octane range from 80.0 to 90.5 motor octane numbers. These samples are analyzed by using the "jack-knife" technique of calibration, wherein the odd numbered samples are placed into a calibration set, and the even numbered samples are used as a prediction set. Regression was performed on the second derivative of the absorbances at these wavelengths using 1220 nm and the olefin absorbance at 2092 nm. The standard error of estimate is 0.362 and the standard error of prediction is 0.412, both in motor octane numbers. Again, this shows excellent agreement with the results obtained by the ASTM method which has a standard error of prediction of 0.600. The results of the analysis are summarized in Table 5.

Example 6

To demonstrate the improvements to be gained from the use of the current invention, a comparison is made between the current invention and values reported by Kelly et. al., in the literature (Analytical Chemistry, 61, p. 313, 1989 [Table VI]). They report results for aromatics, olefins, and saturates (paraffins plus isoparaffins) using short wavelength near infrared and obtain standard errors of calibration of ±0.42, ±0.57, and ±0.73 and multiple correlation coefficients of 0.998, 0.996, and 0.996, for nine gasoline samples using three wavelengths per each PIANO constituent for aromatics, olefins and saturates, respectively.

To compare the current invention to Kelly et. al., nine gasoline samples are selected and analyzed by GC-PIANO and NIR-PIANO. These samples are chosen on the basis of having the greatest range of each PIANO constituent of the gasoline samples. The actual range of constituents values, wavelengths, standard errors of estimate and multiple correlations appear in Table 6. The results in Table 6 show that higher correlations and lower standard errors are seen for the results obtained using the present invention. In fact, for saturates, aromatics, and olefins, the standard errors of the estimate are all decreased by well over 50%.

TABLE 6

PIANO Regression Results Obtained on the Nine Gasoline Samples

| Constituent | Range of Values Vol. % | Wavelengths nm | Std Error of Est. | Mult. Corr. Coefficient |
|---|---|---|---|---|
| Paraffins | 12.9–22.0 | 1894,1230,2124 | 0.0721 | 0.9998 |
| Isoparaffins | 33.7–51.6 | 1220,1289,2400 | 0.0978 | 0.9999 |
| Aromatics | 17.5–39.7 | 1660,2368,2350 | 0.137 | 0.9999 |
| Napthenes | 1.65–10.1 | 1684,2314,1228 | 0.296 | 0.9973 |
| Olefins | 0.823–17.7 | 2092,862,1350 | 0.101 | 0.9999 |
| Saturates | 50.5–66.7 | 1162,2376,2130 | 0.319 | 0.9990 |

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

Reference to copending applications made in the specification is intended to result in such applications being expressly incorporated herein by reference including any patents or other literature references cited within such documents.

What is claimed is:

1. In a process for the control of octane number, or cetane number, of a complex mixture comprising hydrocarbons and/or substituted hydrocarbons, by near infrared spectroscopy, the improvement comprising predicting said octane number, or cetane number by:

a. measuring the near infrared absorbance at at least one wavelength in one or more bands selected from the group consisting essentially of: 1672–1698, 1700–1726, 1622–1650, 1092–1156, 824–884, 1656–1692, 880–974, 1152–1230, 1320–1380, 1470–1578, 1614–1644, 1746–1810, 1940–2000, and/or 2058–2130 nanometers (nm);

b. outputting a periodic or continuous signal indicative of a derivative of said absorbance in said wavelength, or wavelengths in said one or more bands or a combination of mathematical functions comprising a derivative thereof;

c. mathematically converting said signal to an output signal indicative of the octane number or cetane number of said mixture; and d. controlling a blending or other process which correlates with octane number or cetane number by apparatus responsive to said output signal.

2. In a process for the control of octane number, or cetane number of a complex mixture comprising hydrocarbons and/or substituted hydrocarbons by near infrared spectroscopy, the improvement comprising predicting said octane number or cetane number by:

a. measuring the near infrared absorbance at at least one wavelength, in two or more bands selected from the group consisting essentially of: 1672–1698, 1700–1726, 1622–1650, 2064–2234, 1092–1156, 824–884, 1656–1692, 880–974, 1152–1230, 1320–1380, 1470–1578, 1614–1644, 1746–1813, 1940–2000, and/or 2058–2130 nanometers (nm).

b. periodically or continuously outputting a periodic or continuous signal indicative of the intensity of said absorbance in said wavelength, or wavelengths in said two or more bands or a combination of mathematical functions thereof; and c. mathematically converting said signal to an output signal indicative of the octane number or cetane number of said mixture;

d. controlling a blending or other process which correlates with octane number or cetane number by apparatus responsive to said output signal;

wherein said mathematically converting includes taking a first or higher derivative and wherein said output signal is used to control proportioning pumps, automatic control valves, or other flow control means to control the addition rate of each of a series of components fed from different sources to provide a target octane number or, cetane number in a finished blended mixture.

3. A process according to claim 1, or 2, wherein said absorbance is measured at wavelength within the 824–884 nm band.

4. A process according to claim 1, or 2, wherein said absorbance is measured in the 1152–1230 nm band.

5. A process according to claim 1, or 2, wherein said absorbance is measured in the 2064–2234 nm band.

6. A process according to claim 1, or 2, wherein comprising measuring said absorbance in the 880–974 nm band.

7. In a process for the control of octane number, or cetane number of a complex mixture comprising hydrocarbons and/or substituted hydrocarbons by near infrared spectroscopy, the improvement comprising predicting said octane number, or cetane number by:

a. measuring the near infrared absorbance at at least one wavelength, in one or more bands selected from the group consisting essentially of:

1672–1698, 1700–1726, 1622–1650, 1656–1692, 1320–1380, 1470–1578, 1614–1644, 1746–1810, 1940–2000, and/or 2058–2130 nanometers (nm).

b. outputting a periodic or continuous signal indicative of the intensity of said absorbance in said wavelength, or wavelengths in said one or more bands or a combination of mathematical functions thereof; and c. mathematically converting said signal to an output signal indicative of the octane number or cetane number of said mixture, d. controlling a blending or other process which correlates with octane number or cetane number by apparatus responsive to said output signal.

8. A process according to claim 7, wherein said functions comprise a derivative of said absorbance.

9. A process according to claim 1, 7, or 2, wherein said functions are obtained by a process comprising a base line offset correction.

10. A process according to claim 1, 7, or 2 wherein the mixture is a stream and said output signal is indicative of pump octane.

11. A process according to claim 1, 7, or 2 wherein the mixture is a stream and said output signal is indicative of motor octane.

12. A process according to claim 1, 7, or 2 wherein said output signal is indicative of cetane number.

13. A system for blending hydrocarbon and/or substituted hydrocarbon feeds having various values of octane or cetane comprising in combination:

A. NIR absorbance sensing means for emitting a signal indicative of absorbance in at least two bands selected from the group consisting essentially of: 1672–1698, 1700–1726, 1622–1650, 2064–2234, 1092–1156, 824–884, 1656–1692, 880–974, 1320–1380, 1470–1578, 1614–1644, 1746–1810, 1940–2000, and/or 2058–2130 nanometers (nm);

B. computer means for mathematically converting said signal to an output indication of octane or other measure of fuel quality;

C. flow control means responsive to said output, for controlling respective flows of said feeds to produce a blended mixture having substantially a preset value of said octane or cetane.

14. A system according to claim 13 wherein said computer means take a first or higher derivative of said signal.

15. A system according to claim 13 wherein said flow control means controls the flow of streams of two or more components of said mixture.

16. A process according to claim 13 wherein said composition comprises alpha olefins or mixtures thereof.

17. A process according to claim 1, 7, 2, or 13 wherein said hydrocarbons comprise reformer feed, reformate (stabilized and/or unstabilized), fluid catalytic cracker product, alkylate gasoline, polymerization gasoline, isomerate gasoline, and raffinate, or other refinery blending streams or mixtures thereof.

18. A process according to claim 1, 7, 2, or 13 wherein said mixture flows substantially intermittently or continuously past the point of measuring said absorbance.

19. A process according to claim 1, 7, 2, or 13 wherein the mixture is a stream and said output signal is indicative of research octane.

20. A process according to claim 1, 7, 2, or 13 wherein said signal controls a fuel blending system feeding blending components having different octane or cetane into a common zone, whereby a product having a desired octane or cetane is produced.

21. A process according to claim 1, 7, 2, or 13 wherein said complex mixture comprises gasoline.

22. A process according to claim 1, 7, 2, or 13 wherein said complex mixture comprises diesel fuel.

23. A process according to claim 1, 7, 2, or 13 wherein the hydrocarbons and/or substituted hydrocarbons are involved in a chemical reaction.

24. A process according to claim 1, 7, 2, or 13 wherein said mathematically converting step comprises multiple regression analysis.

25. A process according to claim 1, 7, 2, or 13 wherein said mathematically converting step comprises partial least squares analysis.

26. A process according to claim 1, 2, or 13 wherein said absorbance is measured in the 1092–1156 nm band.

27. A process according to claim 1, 7, 2, or 13 wherein said absorbance is measured in the 1320–1380 nm band.

28. A process according to claim 1, 7, 2, or 13 wherein said absorbance is measured in the 1470–1578 nm band.

29. A process according to claim 1, 7, 2, or 13 wherein said absorbance is measured in the 1614–1644 nm band.

30. A process according to claim 1, 7, 2, or 13 wherein said absorbance is measured in the 1746–1810 nm band.

31. A process according to claim 1, 7, 2, or 13 wherein said absorbance is measured in the 1940–2000 nm band.

32. A process according to claim 1, 7, 2, or 13 wherein said absorbance is measured in the 2058–2130 nm band.

33. A processing according to claim 1, 7, 2, or 13 wherein said mathematically converting step comprises principal component regression analysis.

34. In a process for the control of octane number, or cetane number, of a complex mixture comprising hydrocarbons and/or substituted hydrocarbons, by near infrared spectroscopy, the improvement comprising predicting said octane number, or cetane number by:

a. measuring the near infrared absorbance at least one wavelength in one or more bands selected from the group consisting essentially of:
1672–1698, 1700–1726, 1622–1650, 1656–1692, 1320–1380, 1614–1644, 1746–1810, and/or 1940–2000 nanometers (nm);

b. outputting a periodic or continuous signal indicative of a derivative of said absorbance in said wavelength, or wavelengths in said one or more bands or a combination of mathematical functions comprising a derivative thereof;

c. mathematically converting said signal to an output signal indicative of the octane number or cetane number of said mixture; and d. controlling a blending or other process which correlates with octane number or cetane number by apparatus responsive to said output signal.

35. In a process for the control of octane number, or cetane number of a complex mixture comprising hydrocarbons and/or substituted hydrocarbons by near infrared spectroscopy, the improvement comprising predicting said octane number or cetane number by:

a. measuring the near infrared absorbance at at least one wavelength, in two or more bands selected from the group consisting essentially of: 1672–1698, 1700–1726, 1622–1650, 1656–1692, 1320–1380, 1470–1578, 1614–1644, 1746–1810, and/or 1940–2000 nanometers (nm).

b. periodically or continuously outputting a periodic or continuous signal indicative of the intensity of said absorbance in said wavelength, or wavelengths in said two or more bands or a combination of mathematical functions thereof; and c. mathematically converting said signal to an output signal indicative of the octane number or cetane number of said mixture;

d. controlling a blending or other process which correlates with octane number or cetane number by apparatus responsive to said output signal;

wherein said mathematically converting includes taking a first or higher derivative and wherein said output signal is used to control proportioning pumps, automatic control valves, or other flow control means to control the addition rate of each of a series of components fed from different sources to provide a target octane number or, cetane number in a finished blended mixture.

36. A system for blending hydrocarbon and/or substituted hydrocarbon feeds having various values of octane or cetane comprising in combination:

A. NIR absorbance sensing means for emitting a signal indicative of absorbance in at least two bands selected from the group consisting essentially of: 1672–1698, 1700–1726, 1622–1650, 1656–1692, 1320–1380, 1470–1578, 1614–1644, 1746–1810, and/or 1940–2000 nanometers (nm);

B. computer means for mathematically converting said signal to an output indication of octane or other measure of fuel quality;

C. flow control means responsive to said output, for controlling respective flows of said feeds to produce a blended mixture having substantially a preset value of said octane or cetane.

* * * * *